(12) United States Patent
Hecht

(10) Patent No.: US 9,182,419 B2
(45) Date of Patent: Nov. 10, 2015

(54) CONVEYING SYSTEM FOR MATERIAL SAMPLES, ESPECIALLY MEDICAL SAMPLES

(71) Applicant: GLP Systems GmbH, Hamburg (DE)

(72) Inventor: Robert Hecht, Seehausen (DE)

(73) Assignee: GLP Systems GmbH, Hamburg (DE)

( * ) Notice: Subject to any disclaimer, the term of this patent is extended or adjusted under 35 U.S.C. 154(b) by 0 days.

(21) Appl. No.: 14/378,759

(22) PCT Filed: Feb. 11, 2013

(86) PCT No.: PCT/EP2013/052703
§ 371 (c)(1),
(2) Date: Aug. 14, 2014

(87) PCT Pub. No.: WO2013/120810
PCT Pub. Date: Aug. 22, 2013

(65) Prior Publication Data
US 2015/0034461 A1    Feb. 5, 2015

(30) Foreign Application Priority Data
Feb. 15, 2012  (EP) ..................................... 12155634

(51) Int. Cl.
B65G 35/06 (2006.01)
B65G 47/71 (2006.01)
G01N 35/04 (2006.01)

(52) U.S. Cl.
CPC ........ *G01N 35/04* (2013.01); *G01N 2035/0406* (2013.01); *G01N 2035/046* (2013.01); *G01N 2035/0467* (2013.01); *G01N 2035/0475* (2013.01); *G01N 2035/0489* (2013.01)

(58) Field of Classification Search
None
See application file for complete search history.

(56) References Cited

U.S. PATENT DOCUMENTS

| 5,730,276 A | 3/1998 | Itoh | |
|---|---|---|---|
| 6,429,016 B1 | 8/2002 | McNeil | |
| 2004/0109745 A1* | 6/2004 | Wood | 414/346 |
| 2005/0271555 A1 | 12/2005 | Itoh | |
| 2006/0157320 A1* | 7/2006 | Spoeler | 198/463.1 |
| 2009/0078484 A1* | 3/2009 | Kocijan | 180/167 |
| 2010/0239461 A1 | 9/2010 | Itoh | |

FOREIGN PATENT DOCUMENTS

| DE | 4434714 | 4/1996 |
|---|---|---|
| DE | 4434714 A1 | 4/1996 |
| EP | 2074431 | 4/2011 |
| WO | 2011118190 | 9/2011 |

* cited by examiner

*Primary Examiner* — Kavel Singh
(74) *Attorney, Agent, or Firm* — Sand & Sebolt

(57) ABSTRACT

A conveying system for material samples, especially medical samples, comprising a conveyor track forming at least one conveying section and at least one self-propelled sample holder displaceable along the conveying section holding a sample vessel. The holder comprises a drive motor, an energy accumulator for supplying the motor with energy and a friction wheel, drivable by the motor, for transmitting force onto the track. The track has at least one guide structure forming the conveying section. The holder has exactly one wheel on a lower side facing the track in operation, and has at least two sliding elements which rest on the track in operation and slide along the track's surface, the sliding elements and the wheel lying on the vertices of a triangle. The holder, on its lower side, has a guide element for cooperation with the guide structure in the track to guide the holder along the conveying section.

13 Claims, 2 Drawing Sheets

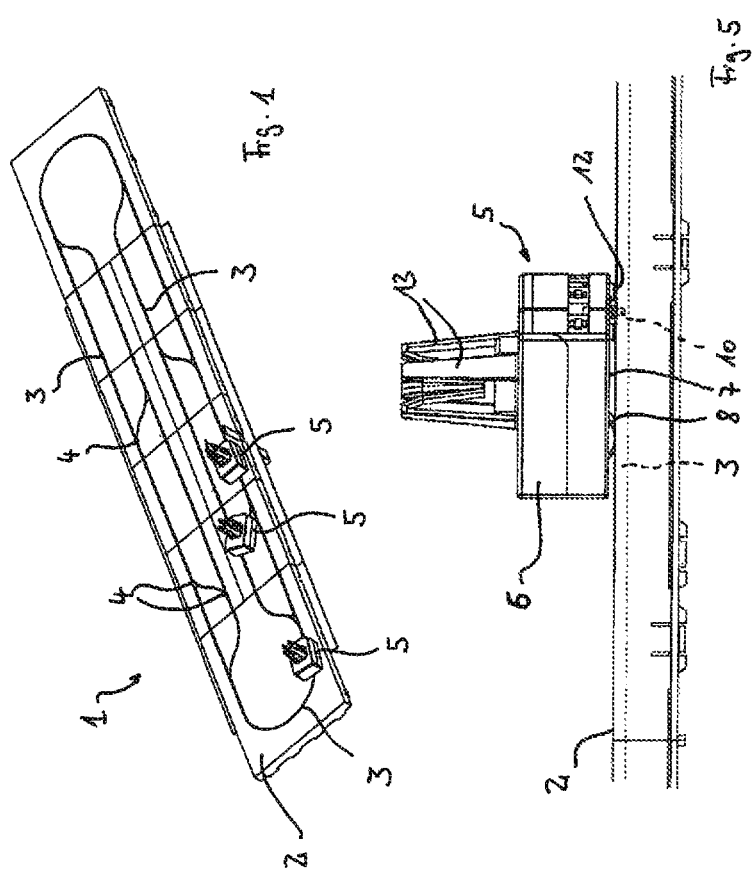

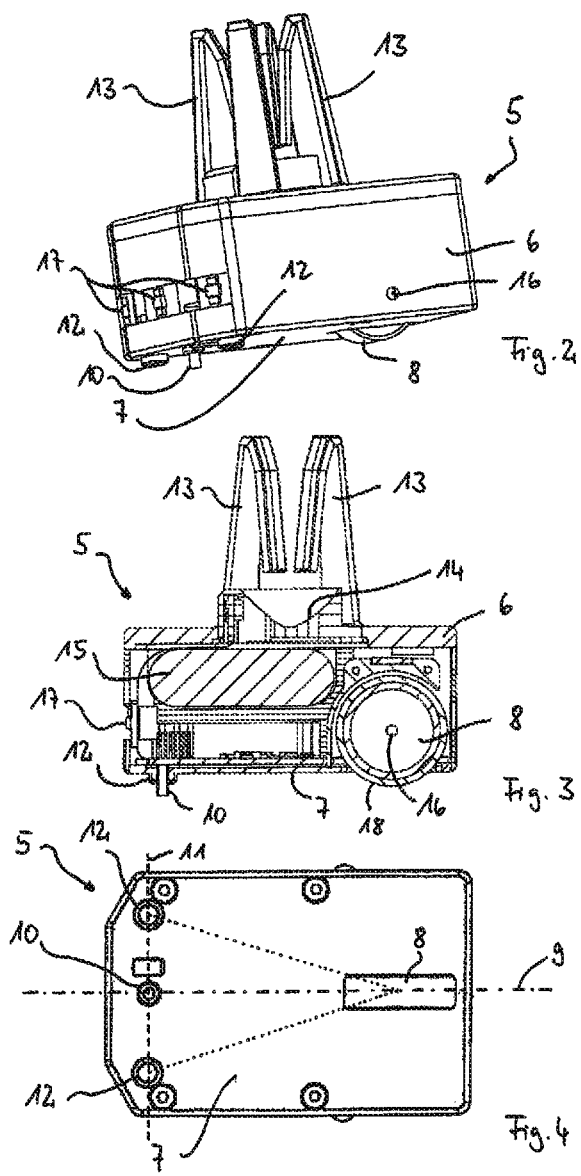

CONVEYING SYSTEM FOR MATERIAL SAMPLES, ESPECIALLY MEDICAL SAMPLES

TECHNICAL FIELD

The invention relates to a conveying system for material samples, in particular medical samples, where the system includes a conveyor track forming at least one conveying section, and with at least one self-propelled sample holder that can be moved along the conveying section and is constructed to receive a sample container, which sample holder comprises a drive motor, an energy store for supplying the drive motor with drive energy, and a friction wheel that can be driven by the drive motor for transferring a drive force to the conveyor track, wherein the conveying section comprises at least one guide structure for forming the conveying section.

PRIOR ART

In the field of analysis of material samples it is frequently necessary to analyze and process a large number of samples in comparatively short time periods. This is especially true in the field of medical samples such as, e.g., samples of body fluids that are examined in medical analysis laboratories with a high degree of automation. The laboratory receives comparatively few post-calculation contributions for the examination of an individual sample, for which reason already, for reasons of cost efficiency and general reasons of economy, a treatment and processing of the medical samples that is highly automated is required in this area and is also already being carried out today.

It is customary here that individual samples are transported in a laboratory system along a conveyor track and are brought to the particular analysis devices provided for their processing and located on the conveyor track. The individual medical samples located on the conveyor track and located on sample holders that can be moved along the conveyor track are necessarily to be subjected to different analyses, either to only one such analysis or, if necessary, even to successive different examinations. Conceivable analyses in respective different analysis devices can be, e.g., in the case of a blood sample, the examination of the hemoglobin value (HB value), of a cholesterol content, of the content of uric acid or of other medicinally relevant parameters. Urine samples can be examined, for example, for their pH, the content of red blood corpuscles, or a general protein content.

Conveying systems, comprising conveyor tracks and sample holders to be transported in them, have long been known already for an appropriate transporting of the sample holders provided with sample containers holding samples. Thus, there are such systems with "passive" sample holders that are moved in the conveyor track without their own drive possibilities with the aid of the conveyor devices located in the conveyor track such as, in particular, conveyor belts or conveyor straps. Examples for such solutions are disclosed in DE 44 34 714 A1 and EP 2 074 431 B1.

However, there is the problem in such conveying systems, in which the drive technology is located in the conveyor tracks, that in the case of a drive failure, as a rule, the entire laboratory system comes to a standstill and cannot be used until a successful maintenance or repair of the conveyor track and of its drive system. Such a standstill of the entire laboratory means at least significant economic damage on account of the high throughput rates to be maintained for the economy of the operation of the laboratory.

In order to avoid this damage, alternative design possibilities help, in which the drive technology is not located in the conveyor track itself but rather in the sample holders, which are designed to move themselves. An example of such a solution for a conveying system is shown in U.S. Pat. No. 6,429,016 B1. In it, self-propelled, three- and/or four-wheel sample holder robots are disclosed that are controlled by guidable wheels and can be moved along conveying sections in the conveyor track to a respective destination location. The sample holder robots shown in it are designed for receiving a plurality of sample containers.

Another example for a conveying system with a sample holders, independently moving in a conveyor track along a conveying section, is disclosed in US 2005/027 1555 A1. In it, sample holders are shown that can move with at least two wheels mounted on a rigid, driven axle. The sample holders shown are provided with a circular base surface and move in U-shaped, tunnel-like tracks open at the top and whose side walls also form a guide for the sample holders. The sample holders disclosed in US 2005/0271555 A1 are constructed to receive a single tubular sample container.

Even if the problem of a long downtime of the entire conveying system and therefore of a laboratory system can be overcome in the case of a malfunction of the drive with the conveying systems disclosed with the last-cited publications U.S. Pat. No. 6,429,016 B1 and US 2005/027 1555 A1 by shifting the drive into the sample holder itself—here, instead of this a sample holder with a defective drive can simply be removed and replaced by a sample holder with a functioning drive, there are still disadvantages and deficiencies with the previously described system that the invention intends to resolve:

Thus, the self-propelled sample holders shown in U.S. Pat. No. 6,429,016 B1 are constructed in a very complex and intricate manner as regards their mechanism with their own steering. This complex and complicated construction renders the individual sample holders, of which a great number are to be used in a laboratory operation, expensive to acquire and at the same time subject to breakdowns.

In the self-propelled sample holders shown in US 2005/027 1555 A1 the mechanical construction of the sample holders is distinctly simpler in comparison to those known from the previously cited publication U.S. Pat. No. 6,429,016 B1, and therefore the individual sample holders are more economical to manufacture and more robust; however, even here problems result. On the one hand, the conveyor track is complex and expensive to manufacture due to the requirement of its U-shaped profile regarding the use of material. Also, the individual sample holders cannot be freely reached in this track but rather it can prove to be complicated, depending on the density of the traffic occurring in the conveyor track, to remove one of the sample holders in a targeted manner from the conveyor track.

Another problem is posed regarding the drive and the guideability. The sample holder in accordance with this publication is not provided with a guidable axle but rather a change of direction is achieved by a guiding by the sidewalls of the track in the manner of a buffer wall. In curve or shunt areas the sample holder travels with a circular diameter against a wall of the guide track or a shunt positioning wall pivoted into the course of the track and travels in this area against the wall or the shunt positioning wall until the rigid drive axle has successively aligned itself vertically to the new direction of travel and the sample holder can again resume travel. This results in significantly slowed-down passage times in areas of curves and shunts, as a result of which the processing speed in the entire system is braked.

Presentation of the Invention

Here, as already mentioned, the present invention wants to make improvements. Therefore, the invention should further develop a conveying system for material samples, in particular medical samples in accordance with the previously known prior art with self-propelled sample holders so that, given sample holders that are constructed in a simple and robust manner at the same time, a reliable and uninterrupted passage through the conveying section is possible, even in the area of curves and shunts, with a secure guiding and section precision.

This problem is solved by a conveying system for material samples, in particular medical samples, wherein the sample holder comprises exactly one wheel on a lower side that faces the conveyor track during operation, which wheel is the friction wheel that can be driven by the drive motor, that the sample holder furthermore comprises at least two sliding elements on the lower side that rest during operation on the conveying section and slide along its surface, wherein the at least two sliding elements and the wheel lie on the end points of a triangle, and that the sample holder comprises a guide element on its lower side for interacting with the guide structure in the conveying section for guiding the sample holder along the conveying section. Advantageous further developments of such a conveying system include that the wheel includes a rigid and non-guidable axle; that that the wheel is located with its longitudinal extension along a central axis of the sample holder; and that the guide element lies on a line along the longitudinal extension of the wheel. Furthermore, the wheel lies, starting from a projection of the center of gravity of the sample holder on its lower side, on a first side of this projection and that the guide element lies on a second, opposite side of this projection. The system further includes a guide groove designed as a guide structure that is constructed in the guide track and extends, transverse to its surface, into its depth, and by a guide pin as the guide element that is located on the lower side of the sample holder and projects from the latter. The sliding elements consist of a material with low sliding friction in comparison to the material of the conveyor track, in particular such a plastic. Additionally, the sample holder has a substantially rectangular base surface, particularly a rectangular base surface with beveled edges on its front end, viewed in the direction of forward travel. Furthermore, the sample holder comprises a receptacle for a single, in particular tubular sample container.

According to the invention the conveying system for material samples, in particular medicinal samples, comprises a conveyor track that forms at least one conveying section. Furthermore, the system comprises at least one self-propelled sample holder that can be moved along the conveying section and is constructed to receive a sample container. This sample holder comprises a drive motor, an energy store for supplying the drive motor with drive energy and a friction wheel, that can be driven by the drive motor, for transferring a drive force to the conveyor track. The conveyor track comprises at least one guide structure for forming the conveying section. In the previously cited features the conveying system in accordance with the invention coincides with those from the prior art. What is novel and characteristic for the invention in the conveying system of the invention is the fact that the sample holder comprises exactly one wheel only, on a lower side facing the conveyor track during operation. This is the friction wheel that can be driven by the drive motor. In addition, the sample holder has at least two sliding elements on the lower side that rest on the conveyor track during operation and slide along its upper surface. The wheel and the at least two sliding elements lie on the end points of a triangle and thus impart a secure stability to the sample holder in order that it can move along the conveying pathway without tipping over on the conveyor track. The guiding along the conveying section is brought about by a guide element located on the lower side of the sample holder and which cooperates with the guide structure in the conveyor track. This combination of guide element and guide structure brings about the setting of the direction for the self-propelled sample holder as regards the direction along which it follows the conveying section. In other words the sample holder is passively guided on the conveyor track by this interaction of the guide structure and guide element.

The implementation of the guiding of the sample holder along the conveying section, by the interaction of the guide element located on the lower side of the sample holder and of the guide structure in the conveyor track, allows the sample holder to be designed comparatively simply and economically in its drive, since no mechanical or control-technology means for an active guidance of the sample holder are provided. Furthermore, the reduction of the number of wheels to a single wheel, namely, the friction wheel that can be driven by the drive motor, brings about a further simplification. In particular in the case of rapid travel in curves or shunts there is always the problem for wheel pairs located along an axle that the wheels running on different curve radii have to rotate at different speeds. If no possibilities for such a different speed of individual wheels on an axle are present to this end (for example, by individual wheel drives, that are complicated to control, or, however, by differentials on the particular wheels), then the sample holder, which is equipped with an appropriate two-wheel axle, has the tendency to escape the conveying section or even to tip over in curve travel or in shunts that are to be passed through.

Therefore, the measure of providing only a single wheel, constructed here as a friction wheel and connected to the drive, has the result, in conjunction with the directional guidance by the guide element and the guide structure, that in the conveying system of the invention the sample holders can travel through corresponding curves or shunts at a comparatively more elevated speed than is possible, for example, in the prior art in accordance with US 2005/027 1555 A1. In this manner, however, the throughput in a conveying system in accordance with the invention can be increased on the whole and/or greater freedom results in the shaping of the conveying sections along the conveyor track.

In order to impart the stability required for the advance to the sample holder at least two sliding elements are located on its lower side that form further support points in addition to the support point of the friction wheel. The stability is achieved by the triangular assembly of the at least two sliding elements and the wheel. The sliding elements should be selected here in such a manner that they cause a slight friction. To this end, appropriate materials are to be selected, in particular those with a low sliding friction in comparison to the material of the conveyor track, for example, such a plastic. Here, plastics such as, e.g., Teflon or comparable low-friction plastics can be considered. In addition, the size of the sliding elements should be kept appropriately small and they can be formed, for example, as spherical sections, as a result of which almost punctiform supports result on the conveyor track.

According to an advantageous further development of the invention, the wheel has a rigid and non-guidable axle. It is basically possible to allocate a passively guided axle to the wheel that tracks the guiding movements that are transferred by the interaction between the guide element and the guide structure onto the sample holder; however, a rigid and non-guidable axle is distinctly simpler and more robust as regards its construction and the mechanics, which results in sample holders with a simpler construction, more economical to produce and are also on the whole more durable and more robust.

The wheel is advantageously located with its longitudinal extension along a central axis of the sample holder. The axis of rotation for the wheel then therefore runs substantially vertical to the central axis. An configuration on the central axis of the sample holder in the cited manner is advantageous since the same travel properties can be achieved therewith for curves and shunts running to the right in the direction of travel as well as for those that run to the left in the direction of travel. Such a configuration also reduces the tipping moments that occur in corresponding curve travel or when traveling through shunts and are to be absorbed by the sliding elements.

Especially favorable guiding properties result when traveling in the conveying section if the guide element is located on a line along the longitudinal extension of the wheel. Therefore, the guide element is located, viewed starting from the wheel, along a direction in which the wheel is rolling. As a consequence, the exerted guiding moments can be readily transferred onto the wheel since the latter can be largely rotated about an axis running vertically through the wheel without causing or requiring a lateral offset or a lateral shifting of the sample holder.

The self-propelled sample holder behaves especially favorably in a conveying system in accordance with the invention if the wheel lies, starting from a position of the center of gravity of the sample holder on its lower side, on a first side of this projection and the guide element lies on a second, opposite side of the projection. Such an arrangement yields an especially stable travel behavior and guidance behavior of the self-propelled sample holder along the conveying section even in curves and shunts.

A preferred embodiment of the guide structure and the guide element consists in that the guide structure is a guide groove extending transversely to the surfaces of the guide track in its depth, and that the guide element is formed by a guide pin located on the lower side of sample holder and projecting from the latter. The guide pin is laterally guided in the guide groove and can slide along the longitudinal direction of this groove. The course of the guide groove then sets the direction for the direction for the travel of the sample holder. The guide pin has, in particular, a circular cross section, so that it can readily retrace the rotary movements of the sample holder relative to the guide groove in curve travel or in shunts. It is preferred that, in the case of a sample holder set into the conveyor track, the guide pin does not extend to the groove bottom of the guide groove so that it does not generate additional friction. However, it can also be desired to allow the guide pin to lie on the groove bottom if it is also one of the sliding elements. However, care must then be taken that an appropriately low friction is formed between the groove bottom and the distal tip of the guide pin.

The sample holder can basically assume any shape suitable for the purposes of the particular conveying system in the concrete design. It is currently preferred, however, that the sample holder has a substantially rectangular base surface. Such a surface proved to be especially simple to create in the production and realization and at the same time to be practical regarding the possible arrangement of the essential elements wheel, sliding elements and guide element on the lower side of the sample holder. It is especially advantageous if the rectangular base surface of the sample holder has beveled edges on the front side, viewed in the direction of forward travel. These beveled edges serve, in particular, for the arrangement of laterally acting sensors with which lateral areas can be monitored during the forward travel in order to avoid collisions.

The conveying system in accordance with the invention comprises in particular a sample holder such that it is constructed for receiving a single, in particular tubular sample container and comprises a corresponding receptacle.

The conveying system of the invention can basically consist of a conveyor track and only a single self-propelled sample holder. However, in practice a plurality of such sample holders come to be used in the conveyor track in order to bring large amounts of samples in the conveying system to the particular target destination and to make possible an automated processing.

SHORT DESCRIPTION OF THE DRAWINGS

Other advantages and features of the invention can be derived from the following description of exemplary embodiments based the attached figures. In the figures:

FIG. 1 shows a schematic view of a possible embodiment of a conveying system in accordance with the invention with a conveyor track, conveying sections formed in the conveyor track and sample holders located therein;

FIG. 2 shows a perspective oblique view from below of a sample holder of the conveying system in accordance with the invention;

FIG. 3 shows a longitudinal section through the sample holder according to FIG. 2;

FIG. 4 shows a view of the sample holder according to FIG. 2 from below; and

FIG. 5 shows a side view of a sample holder set on the conveyor track.

WAY(S) OF IMPLEMENTING THE INVENTION

Different views of the essential components of a conveying system in accordance with the invention are shown in the figures in a possible embodiment. The figures are not complete in the presentation of all details but are limited in the disclosure to the elements essential for the invention. Also, the figures are schematized for the explanation of the elements that are essential here and do not necessarily show the configurations to be optionally selected for a practical realization in a large-scale operation.

FIG. 1 shows a schematic perspective view of a possible design variant of a conveying system 1. The conveying system 1 comprises a conveyor track 2. In the conveyor track 2 guide grooves 3 are 4 embedded in the depth of the conveyor track 2, transverse to its surface, wherein the guide grooves 3 define conveying sections with their courses. The guide grooves 3 are branched onto branches in which shunts are located and are connected in different configurations to each other so that different conveying sections are formed or can be connected depending on the connection of the shunts by connecting different courses of the guide grooves 3.

A total of three self-propelled sample holders 5 are located on the conveyor track 2 in different pathway sections. These sample holders can move themselves along the conveyor track in a manner still to be described in the following.

A sample holder 5 is again shown more closely and in detail in the FIGS. 2 to 4. The sample holder 5 has a base body 6 with a substantially rectangular base surface (cf. FIG. 4). A housing formed by the base body 6 on a lower side 7 of the base body 6 of the sample holder 5 is interrupted by a friction wheel 8. The friction wheel 8 is located (cf. FIG. 4) in its longitudinal extension along a central axis 9 of the sample holder 5. It is located, starting from a projection of a center of gravity of the sample holder 5, on a first side shown on the right in FIG. 4. A guide pin 10 extending vertically from the lower side 7 downward is located opposite the friction wheel 8, which pin is also located on the central axis 9 and to this extent is aligned with the longitudinal extension of the friction wheel 8. As can be recognized in FIG. 4, the guide pin 10 is located on a side of the projection of the center of gravity, which side is diametrically opposite the position of the friction wheel 8, and which side is located between these two elements (not shown in FIG. 4). Two sliding elements 12 projecting from the lower side 7 are located on both sides of the guide pin 10 along a line 11 running substantially vertically to the central axis 9. These sliding elements 12 consist of a material that has a slight sliding friction opposite the material of the surface of the guide track 2 and is formed, e.g., from an appropriate plastic such as, e.g., Teflon.

A receptacle for a single sample container, in particular a tubular sample container is formed by holding fingers 13 on the upper side of the sample holder 5 opposite the lower side 7. A tubular sample container can be introduced between the holding fingers 13 down to the bottom of a cup-shaped receptacle 14.

As can be recognized in FIG. 3, an energy store such as a storage battery accumulator 15 is located inside the base 6 of the sample holder 5. This storage battery feeds the drive motor (not shown in FIG. 3), by means of which the friction wheel 8 can be put in rotation for supplying the travel drive of the sample holder 5 with energy and also supplies other electrical loads located on the sample holder 5 such as, e.g., spacing sensors 17 that serve to monitor a warning for a collision.

The friction wheel 8 is provided along its circumference with a friction lining 18 that serves for the transfer of the force of the advance force onto the surface of the conveyor track 2 in order to ensure the advance of the sample holder 5. During this time the friction wheel 8 rotates about an axle 16 that is rigid and is not a guidable axle.

Finally, it can be recognized in FIG. 4 that the sliding elements (here their middle points) and the friction wheel (here its middle point) are located on the corner points of a triangle (the dotted lines are sketched in to this end), wherein this triangle is an equilateral triangle here. The sliding elements 12 are set to the maximum into the outer corners opposite the friction wheel 8 in order to impart the widest possible expanded support and high stability to the sample holder 5 resting during operation on the conveyor track 2 on the friction wheel 8 and on the two sliding elements 12.

Finally, it can be recognized in FIG. 5 how the sample holder 5 is seated during operation on the conveyor track 2, wherein the guide pin 10 extends into the guide groove 3 and supplies guidance along the conveying section to the self-propelled sample holder 5. The guide pin 10 does not extend to the bottom of the guide groove 3 but rather lies with its distal end free. Therefore, the sample holder 5 rests only on three support points on the conveyor track 2, namely, the two sliding elements 12 and the friction wheel 8. The friction wheel 8 runs, when traveling straight ahead, on the guide groove 3 on account of the alignment with the guide pin 10, for which reason it is constructed to be wider than the width of the guide groove 3 so that it extends to a sufficient extent over the guide groove 3 at the edges in order to form a stable support and in order to be able to transfer, at the same time, a sufficient driving force onto the surface of the conveyor track 2.

In the normal forward travel of the sample holder 5 the friction wheel 8, which is supported in the rear in this direction of travel, pushes the body 6 of the sample holder 5 in the forward direction, wherein the front end of the sample holder 5 rests on the sliding elements 12 and slides over them in the conveyor track 2. If the sample holder 5 now passes into the area of a shunt or a curve, the guide pin 10 follows the corresponding direction of the guide groove and therefore entrains the front end of the storage container 5 with itself. This generates a rotary movement about which the sample holder 5 is rotated on the support point of the friction wheel 8. As a consequence of the fact that only one wheel, the friction wheel 8, is present on the sample holder 5, no problems occur here due to transverse forces produced by different path lengths of an axle wheel on an axle running outside or inside in the curve. Accordingly, no extensive technical measures are required here to decouple such wheels of an axle as regards their rotational speeds and also no problems result like those that can occur in wheels rigidly supported on an axle, especially as regards a reduced speed when passing through curves or shunts. The latter can be traveled through at a distinctly higher speed in the conveying system in accordance with the invention by the sample holders 5 constructed with only one wheel, as described, which results in an, on the whole, elevated throughput in the conveyor track 2. Therefore, in a conveying track 2 more sample holders 5, and therefore samples, can travel through per time unit or, however, in the case of a conveyor track 2 with a certain throughput capacity, a more comprehensive construction with a greater plurality of waiting positions and parking areas can be eliminated and the track system can be constructed to be more compact and smaller.

The shown self-propelled sample holder 5 in accordance with the invention can of course also travel "backwards", that is, in the reverse direction so that the friction wheel 8 then pulls the base body 6 and with it the sample holder 5.

LIST OF REFERENCE NUMERALS 1 conveying system
2 conveyor track
3 guide groove
4 shunt
5 sample holder
6 base body
7 lower side
8 friction wheel
9 central axis
10 guide pin
11 line
12 sliding element
13 holding finger
14 receptacle
15 storage battery
16 axle
17 spacing sensor
18 friction lining

The invention claimed is:
1. A conveying system for material samples comprising:
a conveyor track forming at least one conveying section, and with at least one self-propelled sample holder movable along the conveying section and constructed to receive a sample container, which sample holder comprises a drive motor, an energy store for supplying the drive motor with drive energy, and a friction wheel drivable by the drive motor for transferring a drive force to the conveyor track, wherein the conveying section comprises at least one guide structure for forming the conveying section, and wherein the sample holder com- prises exactly one wheel on a lower side that faces the conveyor track during operation, which wheel is a friction wheel that is drivable by the drive motor, and wherein the sample holder furthermore comprises at least two sliding elements on the lower side that rest during operation on the conveying section and slide along the conveying section's surface, wherein the at least two sliding elements and the wheel lie on end points of a triangle, and wherein the sample holder comprises a guide element on the sample holder's lower side for interacting with the guide structure in the conveying section for guiding the sample holder along the conveying section.

2. The conveying system according to claim 1, wherein the wheel includes a rigid and non-guidable axle.

3. The conveying system according to claim 1, wherein the wheel is located with the wheel's longitudinal extension along a central axis of the sample holder.

4. The conveying system according to claim 3, wherein the guide element lies on a line along the longitudinal extension of the wheel.

5. The conveying system according to claim 1, wherein the wheel lies, starting from a projection of the center of gravity of the sample holder on its lower side, on a first side of this projection and that the guide element lies on a second, opposite side of this projection.

6. The conveying system according to claim 1, further comprising a guide groove designed as a guide structure that is constructed in the guide track and extends, transverse to the guide track's surface, into the guide track's depth, and by a guide pin as the guide element that is located on the lower side of the sample holder and projects from the latter.

7. The conveying system according to claim 1, wherein the sliding elements are comprised of a material with low sliding friction in comparison to the material of the conveyor track.

8. The conveying system according to claim 1, wherein the sample holder has a substantially rectangular base surface.

9. The conveying system according to claim 7, wherein the sample holder has a rectangular base surface with beveled edges on the sample holder's front end, viewed in the direction of forward travel.

10. The conveying system according to claim 1, wherein the sample holder comprises a receptacle for a single sample container.

11. The conveying system according to claim 1, wherein the system is adapted to convey medical samples.

12. The conveying system according to claim 7, wherein the sliding elements are comprised of plastic.

13. The conveying system according to claim 10, wherein the sample holder comprises a receptacle for a tubular sample container.

* * * * *